US012800446B2

(12) United States Patent
Bondi

(10) Patent No.: US 12,800,446 B2
(45) Date of Patent: Nov. 17, 2026

(54) REMOTE FLUID SAMPLING

(71) Applicant: FLUID TRANSFER TECHNOLOGY PTY LTD, Kewdale (AU)

(72) Inventor: Jason Michael Bondi, Kewdale (AU)

(73) Assignee: FLUID TRANSFER TECHNOLOGY PTY LTD, Kewdale (AU)

( * ) Notice: Subject to any disclaimer, the term of this patent is extended or adjusted under 35 U.S.C. 154(b) by 312 days.

(21) Appl. No.: 18/839,738

(22) PCT Filed: Mar. 1, 2023

(86) PCT No.: PCT/AU2023/050137
§ 371 (c)(1),
(2) Date: Aug. 20, 2024

(87) PCT Pub. No.: WO2023/164743
PCT Pub. Date: Sep. 7, 2023

(65) Prior Publication Data

US 2025/0172459 A1 May 29, 2025

(30) Foreign Application Priority Data

Mar. 2, 2022 (AU) ................................ 2022900498

(51) Int. Cl.
*G01N 1/20* (2006.01)
*G01F 11/02* (2006.01)
(Continued)

(52) U.S. Cl.
CPC ......... *G01N 1/2035* (2013.01); *G01F 11/021* (2013.01); *G01F 15/063* (2013.01);
(Continued)

(58) Field of Classification Search
CPC ...... G01N 1/2035; G01N 1/10; G01N 1/2042; G01N 33/2888; G01N 2001/002;
(Continued)

(56) References Cited

U.S. PATENT DOCUMENTS 3,625,655 A 12/1971 Culp et al.
4,018,565 A 4/1977 Fletcher, III et al.

FOREIGN PATENT DOCUMENTS

CN 101533003 A 9/2009
CN 101539565 A 9/2009
(Continued)

OTHER PUBLICATIONS

DE-102019135704-A1, English Translation (Year: 2021).*

*Primary Examiner* — Ryan D Walsh
(74) *Attorney, Agent, or Firm* — Cherskov Flaynik & Gurda, LLC

(57) ABSTRACT

Provided is a remote fluid sampler for sampling fluid, such as oil, from machinery (8). The sampler comprises inlet and outlet port (12) and (14) with a fluid circuit (16) defined therebetween. Fluid sampler also include a 4-way diverter control valve (18), a fluid meter (20), a normally-open (NO) control valve (22) arranged in parallel with a normally-closed (NC) control valve (24) for dynamic fluid flow regulation, and a plurality of check valves (26) for passive fluid flow regulation through the fluid circuit (16). Also included is a sampling port (28) for receiving a metered dose of fluid, and a controller (32) arranged in signal communication with the fluid meter, 4-way diverter and control valves and configured to perform a user-configurable control regime comprising a flush cycle and a meter cycle wherein the sampler facilitates flushing of fluid through the fluid circuit to allow collection of a homogeneous fluid sample from the machinery, in use.

20 Claims, 4 Drawing Sheets

(51) Int. Cl.
*G01F 15/063* (2022.01)
*G01N 1/00* (2006.01)
*G01N 1/10* (2006.01)
*G01N 33/28* (2006.01)

(52) U.S. Cl.
CPC ............. *G01N 1/10* (2013.01); *G01N 1/2042* (2013.01); *G01N 33/2888* (2013.01); *G01N 2001/002* (2013.01); *G01N 2001/1031* (2013.01); *G01N 2001/205* (2013.01)

(58) Field of Classification Search
CPC ...... G01N 2001/1031; G01N 2001/205; G01F 11/021; G01F 15/063
See application file for complete search history.

(56) References Cited

FOREIGN PATENT DOCUMENTS

DE 102010004917 A1 7/2011
DE 102019135704 A1 * 6/2021 ............... G01N 1/10

* cited by examiner

REMOTE FLUID SAMPLING

TECHNICAL FIELD

This invention broadly relates to sampling of machinery fluids, such as oil, and more particularly to a remote fluid sampler and a remote fluid sampling system.

BACKGROUND ART

The following discussion of the background art is intended to facilitate an understanding of the present invention only. The discussion is not an acknowledgement or admission that any of the material referred to is or was part of the common general knowledge as at the priority date of the application.

Proper lubrication of machinery is essential and a significant contributor to the effectiveness and lifetime thereof. It is estimated that around 75% of all machinery bearing failures are due to lubrication issues. For this reason, proper and timely analysis of lubricating oils, greases and hydraulic fluids is essential to ensure problem-free machinery operation. Effective monitoring of such fluids also allows maintenance to be scheduled efficiently, minimising the risk of damage to expensive plants and avoiding unscheduled downtime.

For example, engine oil is an essential consumable in most internal combustion (IC) engines. In an IC engine, both oil and coolant are typically circulated in a closed loop system lubricating and cooling vital parts of the engine. Apart from lubricating, engine oil also performs other functions such as transferring contaminants, sealing of combustion chambers and cooling of moving parts. Oil filters are commonly used to capture and contain most of the unwanted debris in the oil flow.

Both engine oil and filters are typically changed at recommended oil-drain intervals set by machinery and manufacturer specifications. If not properly monitored, oil degradation may lead to corrosion and deposit formation that could lead to loss in efficiency, increased filter restriction, engine reliability issues or even catastrophic failure.

For optimal results, machinery fluids such as oil should be sampled at regular intervals to monitor machinery health and performance. Ideally, oil samples should be taken when an engine is at operating temperature and during operation to provide an accurate indication of operation and to ensure a homogeneous sample is collected. Such 'live' sampling presents specific hazards, particularly in industrial and mining environments.

Applicant has identified shortcomings with conventional sampling practices, where 'live' sampling presents danger to personnel. In particular, sampling of machinery in remote locations, such as mine sites, is difficult due to hazards to personnel as well as communication challenges. In addition, further shortcomings exist with collecting useful samples, as collecting stagnant oil which may contain contaminants, debris, sludge, etc. may misrepresent the oil flowing through machinery, negating the sampling process.

The current invention was conceived with these shortcomings in mind.

SUMMARY OF THE INVENTION

The skilled addressee is to appreciate that reference herein to 'machinery' generally comprises non-limiting reference to mechanical and related utilitarian contrivances configured or adapted to perform a specific function, with such machinery including operating fluids such as oil, coolant, fuels and/or the like. Some non-exhaustive examples of such machinery include internal combustion engines, power generators, gearboxes, compressors, hydraulic cylinders and actuators.

According to a first aspect of the invention there is provided a remote fluid sampler for sampling fluid, such as oil, from machinery, said sampler comprising:

- an inlet and an outlet port via which said sampler is arrangeable in fluid flow communication with said machinery, a fluid circuit defined between said inlet and outlet ports;
- a 4-way diverter control valve configured to control a direction of fluid flow along such fluid circuit;
- a fluid meter configured to capture a metered dose of fluid from said fluid circuit;
- a normally-open (NO) control valve arranged in parallel with a normally-closed (NC) control valve to regulate dynamically fluid flow through the fluid circuit;
- a plurality of check valves arranged to regulate passively fluid flow through the fluid circuit;
- a sampling port configured to receive a sampling reservoir for receiving a metered dose of fluid; and
- a controller arranged in signal communication with the fluid meter, 4-way diverter and control valves and configured to perform a user-configurable control regime comprising:
  - i. a flush cycle by selectively controlling the 4-way diverter and control valves to define a first fluid path along a portion of the fluid circuit which flushes the fluid meter and bypasses the sampling port; and
  - ii. a meter cycle by selectively controlling the fluid meter, 4-way diverter and control valves to define a second fluid path along the fluid circuit which allows the fluid meter to collect fluid from the fluid circuit and thereafter dispense such a metered dose of said collected fluid to the sampling port;

wherein the sampler facilitates flushing of fluid through the fluid circuit to allow collection of a homogeneous fluid sample from the machinery, in use.

In an embodiment, the controller comprises a wireless transceiver for sending and receiving signals to and from a remote computer system.

In an embodiment, the wireless transceiver comprises a cellular modem configured to establish a dedicated communications protocol between the sampler and the remote computer system.

In an embodiment, the fluid meter comprises a fluid cylinder with a reciprocating piston therein, said piston configured to slidably displace due to fluid pressure in the fluid circuit from the machinery to capture a metered dose of fluid during the meter cycle.

In an embodiment, the fluid meter comprises a fluid cylinder with a reciprocating piston therein, an actuator configured to slidably displace said piston in the cylinder to capture a metered dose of fluid.

Typically, the actuator of the reciprocating piston is controlled by the controller in accordance with the control regime.

In an embodiment, the fluid meter is controlled by the controller in accordance with the control regime.

In an embodiment, the controller includes a fluid characteristic sensor arranged in the fluid circuit and responsive to characteristics of the sampled fluid.

In an embodiment, the fluid characteristic sensor is responsive to fluid characteristics selected from a non-exhaustive list consisting of temperature, viscosity, pressure, oxidation, acidity or basicity, permittivity, opacity and impedance, i.e. a gamut of tribology characteristics as related to machinery.

In an embodiment, the controller is configured to transmit sensed fluid characteristics to the remote computer system via the transceiver.

In an embodiment, the control regime comprises control functions selected from a non-exhaustive group consisting of sampling intervals, sampling frequency, volume of metered dose, transmission of sensed fluid characteristics, control errors and sampler health.

In an embodiment, the flush cycle of the control regime includes the controller sensing the fluid characteristics in the fluid circuit, the meter cycle only performed once predetermined sensed fluid characteristics are constant for a predetermined period of time.

In an embodiment, the controller is configured to receive an update to the control regime from the remote computer system via the transceiver.

In an embodiment, the controller includes a sampling reservoir presence sensor to sense a presence of a received sampling reservoir at the sampling port, the controller configured to only perform the meter cycle if a sampling reservoir is present.

In an embodiment, the 4-way diverter control valve comprises a 4-way 3-position spool diverter valve.

In an embodiment, the control valves for dynamic fluid flow regulation comprises solenoid valves.

In an embodiment, the check valves for passive fluid flow regulation comprises soft-seat check valves.

In an embodiment, the sampler comprises a sealed enclosure with a pressuriser configured to generate a positive air pressure withing said enclosure to impede ingress of contaminants.

In an embodiment, the second fluid path, as defined by the controller via the control regime, comprises a meter fluid path which allows the fluid meter to collect fluid from the fluid circuit and a dispense fluid path whereby the fluid meter dispenses such collected fluid to the sampling port.

According to a second aspect of the invention there is provided a remote fluid sampling system comprising:

- machinery including a remote fluid sampler in accordance with the first aspect of the invention; and
- a remote computer system;

wherein a wireless transceiver of said fluid sampler operatively establishes a dedicated communications protocol between the sampler and the remote computer system; and wherein a controller of the fluid sampler performs a control regime to facilitate flushing of fluid through a fluid circuit of the sampler to allow subsequent collection of a homogeneous fluid sample from the machinery, in use.

According to a further aspect of the invention there is provided a remote fluid sampler and a remote fluid sampling system, substantially as herein described and/or illustrated.

BRIEF DESCRIPTION OF THE DRAWINGS

The description will be made with reference to the accompanying drawings in which.

DETAILED DESCRIPTION OF EMBODIMENTS

Figure 1:
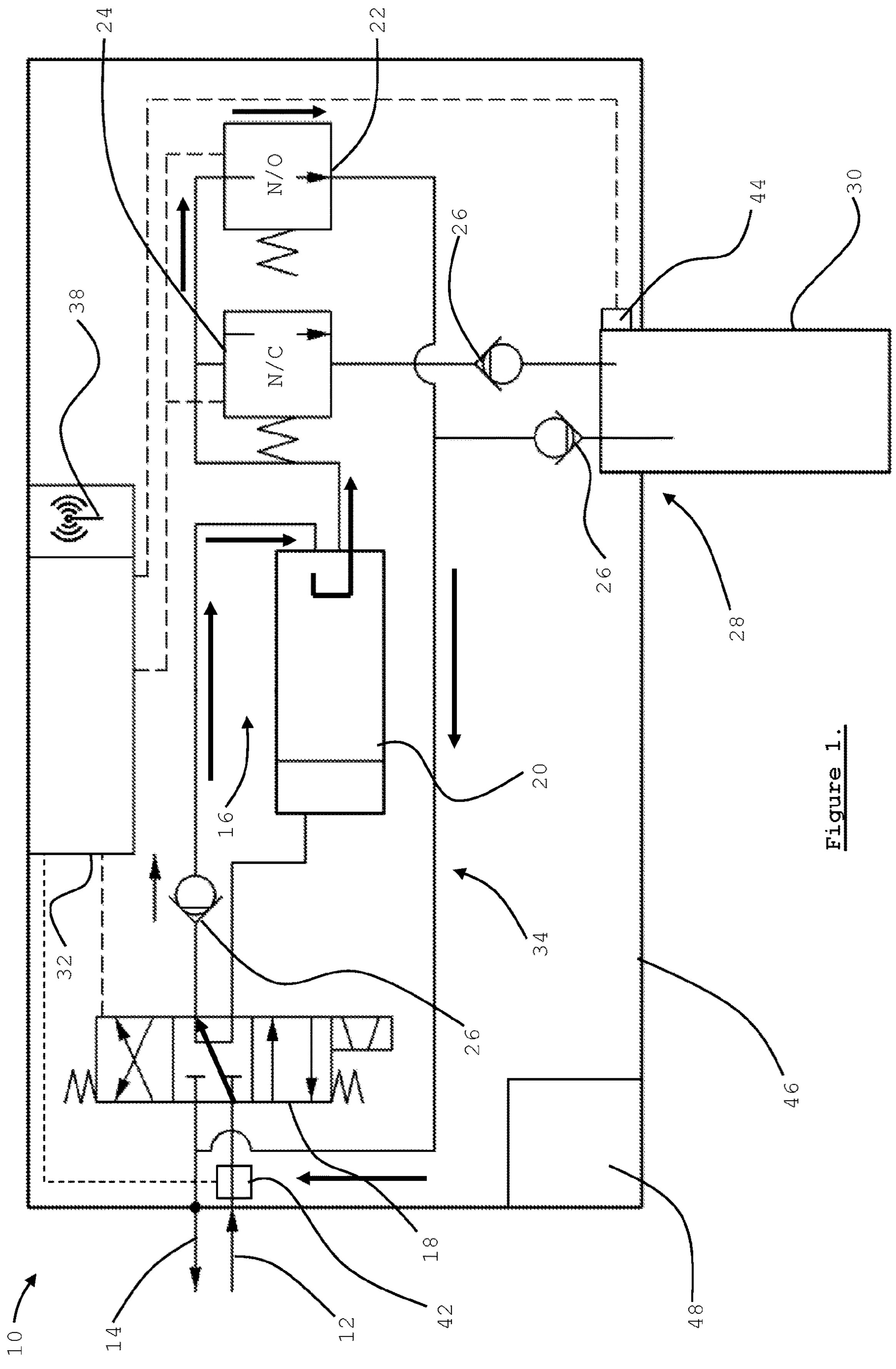
FIG. 1 is a schematic representation of an embodiment of a remote fluid sampler for sampling fluid, such as oil, from machinery, in accordance with an aspect of the present invention, the sampler showing fluid flow during a flush cycle via a first fluid path.

Further features of the present invention are more fully described in the following description of several non-limiting embodiments thereof. This description is included solely for the purposes of exemplifying the present invention to the skilled addressee. It should not be understood as a restriction on the broad summary, disclosure or description of the invention as set out above.

In the figures, incorporated to illustrate features of the example embodiment or embodiments, like reference numerals are used to identify like parts throughout. Additionally, features, mechanisms and aspects well-known and understood in the art will not be described in detail, as such features, mechanisms and aspects will be within the understanding of the skilled addressee.

With reference now to the accompanying figures, there is broadly exemplified a remote fluid sampler 10, as well as an associated system 50 for remote fluid sampling. Typically, such a fluid sampler 10 is useable in sampling fluids, such as oil, from machinery 8, including an internal combustion engine 8.1 in some examples. Of course, other machinery requiring fluids, such as lubricant, fuel, coolant, etc. may also be apposite, including gearboxes, hydraulic systems, or the like.

In developing the fluid sampler 10, Applicant has identified a number of shortcomings in the field, including the ability to extract homogenous fluid samples indicative of operating conditions of the machinery 8. For example, sampling of fluid not indicative of an overall or homogenous sample can provide false readings. For this reason, fluid sampler 10 incorporates a specific flush cycle to facilitate such homogenous fluid sample collection.

Additionally, fluid sampler 10 may find particular use in sampling fluid from industrial and mining machinery, such as haul trucks, diggers, etc., that typically operate in remote and harsh conditions. In such mining conditions, for example, mine sites often have a communications network to facilitate monitoring and control of equipment. However, it is very common for such mine site networks to incorporate strict security measures to ensure information is secure. For this reason, mine sites and operators often do not allow service providers access to their networks, making information exchange difficult. The fluid sampler 10 generally incorporates a transceiver 38 which establishes a dedicated network protocol with a remote computer system 40, as required. This functionality obviates the requirement for access to a private communications network.

A further shortcoming identified by the Applicant in the development of fluid sampler 10 is potential sample contamination and/or fluid leakage results from the use of check valves in pressurised fluid systems, as well as contaminant ingress into sampling equipment. For this reason, fluid sampler 10 comprises a specific arrangement of passive and active valves with an associated control regime configuring a fluid circuit with fit-for-purpose fluid paths in order to take fluid samples, as well as minimise leakage and facilitate venting of gases, and the like. Such a fluid circuit 16 may be free-flowing when the sampler 10 is not active during a meter cycle to remove a requirement for valves and check valves that must counteract fluid pressures in an ongoing passive state to prevent leakages, or the like, e.g. a flush cycle is continuously performed unless a meter cycle is performed, as described below. Of course, variations hereon are possible and expected.

Homogeneity of collected or captured fluid samples can be further improved via the inclusion of a fluid characteristic sensor 42 enabling a controller 32 of the fluid sampler 10 to detect sample constancy before or when a sample is taken. Such functionality together with fluid flushing prior to sampling has been found to improve fluid sampling.

In a typical example, as shown in FIG. 1, the remote fluid sampler 10 for sampling fluid, such as oil, from machinery 8 generally comprises an inlet port 12 and an outlet port 14 via which said sampler 10 is arrangeable in fluid flow communication with said machinery 8. For example, fluid sampler 10 may be arranged within a lubricating system of an internal combustion engine 8.1, or the like. A fluid circuit 16 is defined between said inlet and outlet ports 12 and 14 to allow fluid, such as oil, to flow through fluid sampler 10, as described in more detail below.

In the exemplified embodiment, fluid sampler 10 includes a 4-way diverter control valve 18 which is configured to control a direction of fluid flow along the fluid circuit 16 defined between the inlet and outlet ports 12 and 14. In an embodiment, the 4-way diverter control valve 18 may comprise a 4-way 3-position spool diverter valve, or the like. Fluid sampler 10 also includes a fluid meter 20 which is configured to capture a metered dose of fluid from said fluid circuit 16 during a meter cycle.

The fluid meter 20 typically comprises a fluid cylinder with a reciprocating piston therein, said piston configured to slidably displace due to fluid pressure in the second fluid path from the machinery to capture a metered dose of fluid during the meter cycle. In another embodiment, the fluid meter 20 may also include a fluid cylinder with a reciprocating piston therein, with a suitable actuator configured to slidably displace said piston in the cylinder to capture a metered dose of fluid and/or return the piston to a pre-meter position. In this manner, a suitably configured fluid meter 20 is able to capture precise and metered doses of fluid, as required.

In the exemplified embodiment, fluid sampler 10 further includes a normally-open (NO) control valve 22 arranged in parallel with a normally-closed (NC) control valve 24, as shown, with said valves 22 and 24 positioned in the fluid circuit 16 to regulate dynamically fluid flow through the fluid circuit 16, i.e. valves 22 and 24 are controllable via a suitable controller 32 to open or close dynamically depending on requirements. Such control valves 22 and 24 for dynamic fluid flow regulation are typically solenoid valves, or the like. The specific parallel configured of the NO and NC valves 22 and 24 facilitates in minimising fluid leakage and uncontrolled fluid flow through the fluid circuit 16.

Additionally, fluid sampler also 10 includes a plurality of check valves 26 that are specifically arranged within the fluid circuit 16 to regulate passively fluid flow through the fluid circuit 16, e.g. soft-seat check valves, or the like. The skilled addressee will appreciate that such check valves 26 are passive components and are positioned in said fluid circuit 16 to provide the functionality required, as described and illustrated herein.

Fluid sampler 10 further includes a sampling port 28 which is configured to receive a sampling reservoir 30 for receiving a metered dose of fluid. Such a sampling port 28 is typically a threaded connection to receive a complementarily threaded sampling reservoir 30, such as a sample bottle, or the like, therein.

Importantly, fluid sampler 10 includes a controller, such as a programmable logic controller (PLC) or similar microcontroller, which is arranged in signal communication with the fluid meter 20, 4-way diverter 18 and control valves 22 and 24 and which is configured to perform a user-configurable control regime. Such a control regime generally comprises a flush cycle wherein the controller 32 selectively controls the 4-way diverter 18 and control valves 22 and 24, as required, to define a first fluid path 34 along the fluid circuit 16 which flushes the fluid meter 20 and bypasses the sampling port 28, as shown in FIG. 1.

Figure 2:
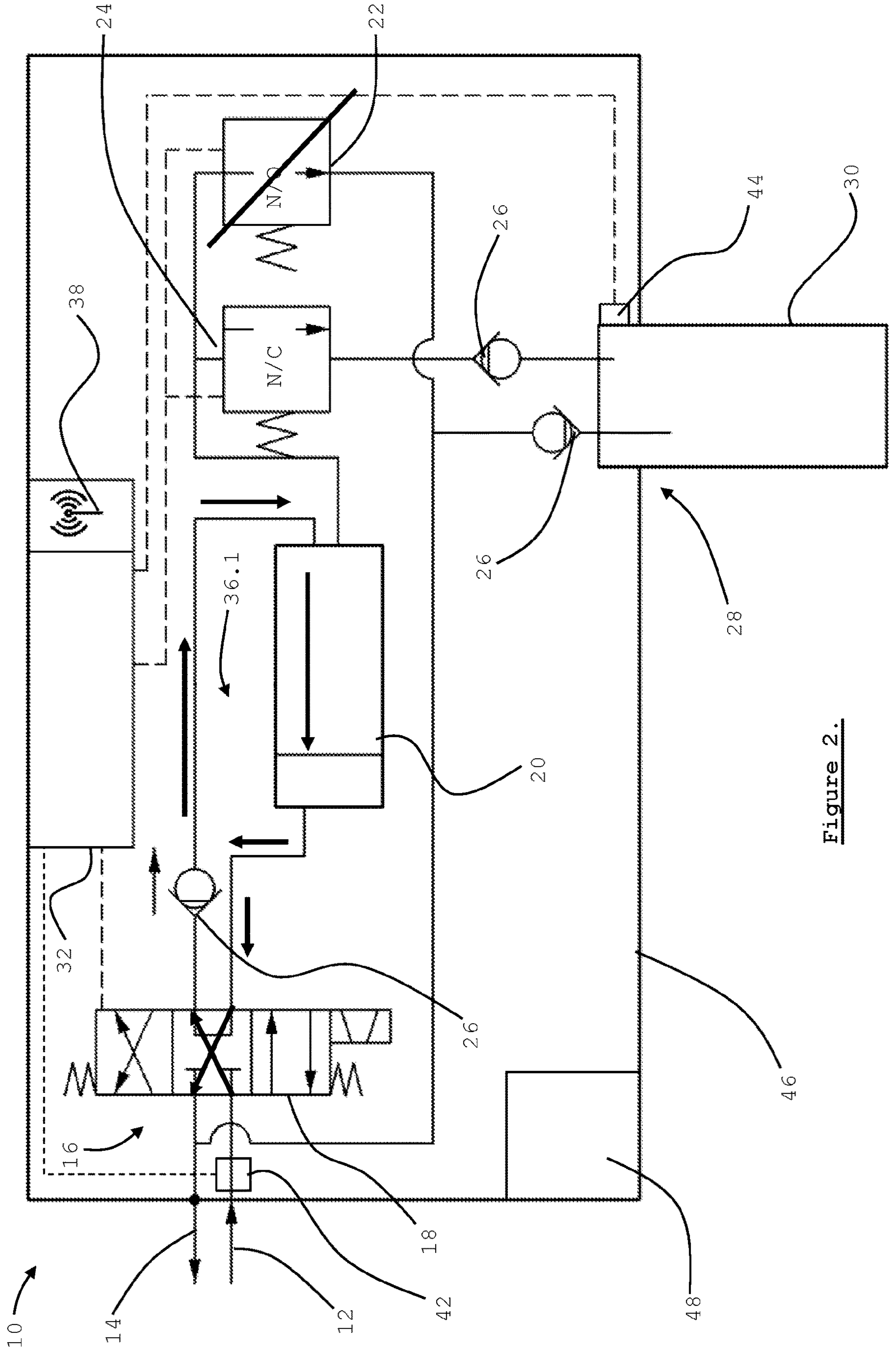
FIG. 2 is a schematic representation of the remote fluid sampler of FIG. 1 showing fluid flow during a meter cycle via a second fluid path.
Figure 3:
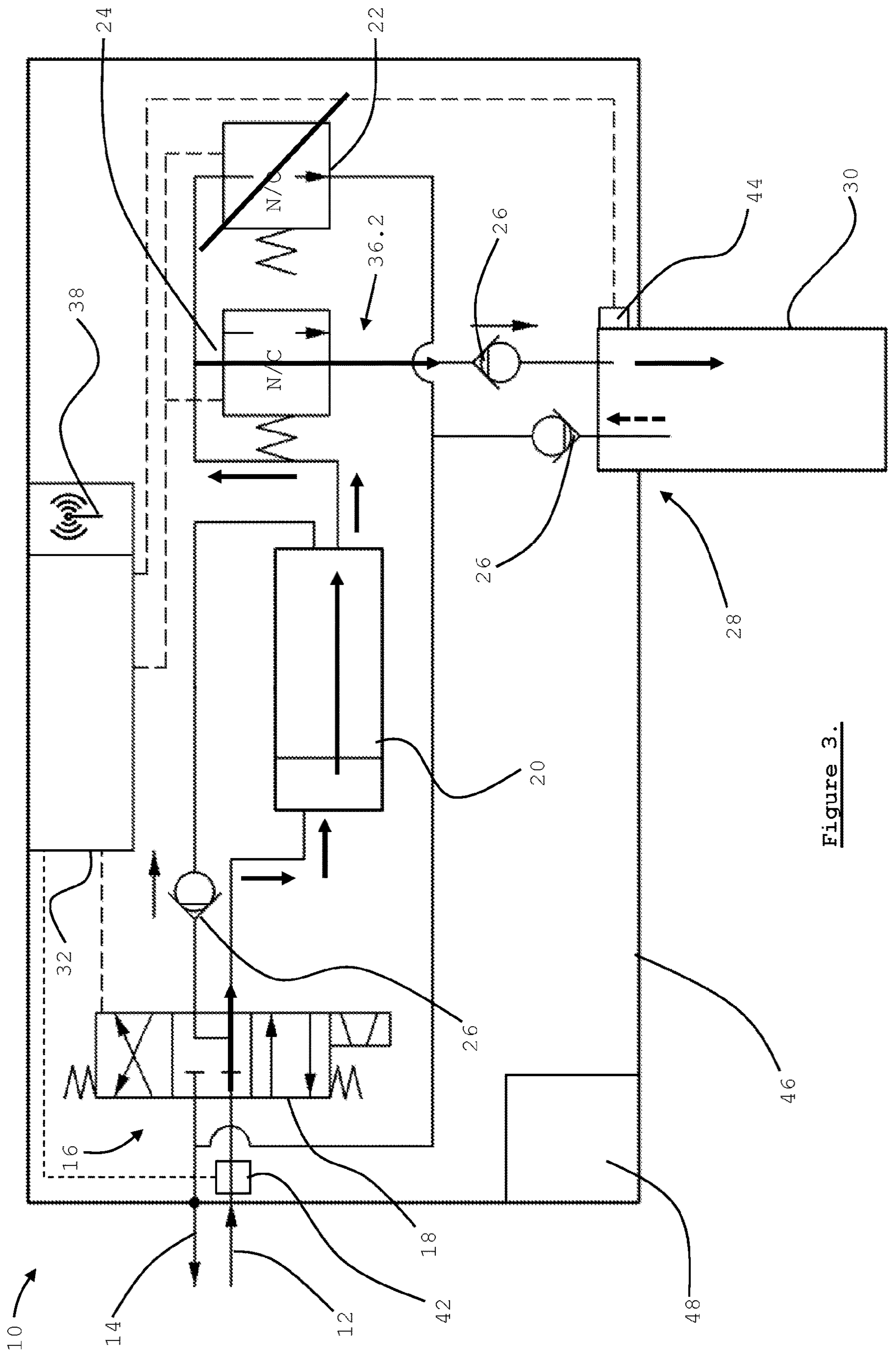
FIG. 3 is a schematic representation of the remote fluid sampler of FIG. 2 showing fluid flow as a metered dose of collected fluid is dispensed to a sampling port.

As shown in FIG. 2, the control regime of the controller 32 also includes a meter cycle wherein said controller 32 selectively controls the fluid meter 20, 4-way diverter 18 and control valves 22 and 24, as required, to define a second fluid path 36 along the fluid circuit 16 which allows the fluid meter 20 to collect fluid from the fluid circuit 16. After such collection of a metered dose of fluid, the meter cycle includes dispensing the metered dose of said collected fluid to the sampling port 28, as indicated in FIG. 3.

In one embodiment, the second fluid path 36, as defined by the controller 32 via the control regime, comprises a meter fluid path 36.1 which allows the fluid meter 20 to collect fluid from the fluid circuit 16, typically under pressure from the machinery 8, as well as a dispense fluid path 36.2 whereby the fluid meter 20 dispenses such collected fluid to the sampling port 28. In this manner, with controller 32 performing or executing such a control regime with flush and meter cycles, the fluid sampler 10 generally facilitates flushing of fluid through the fluid meter 20 before a metered sample is captured to allow collection of a homogeneous fluid sample from the machinery 8, in use.

For example, FIG. 1 shows the controller 32 performing the flush cycle by selectively controlling the 4-way diverter 18 and control valves 22 and 24 to define the first fluid path 34 along the fluid circuit 16. Passive check valves 26, via their respective specific positions within the fluid circuit 16, facilitates such definition of the first fluid path 34, as shown.

Similarly, FIG. 2 shows the controller 32 performing the meter cycle by selectively controlling the fluid meter 20, 4-way diverter 18 and control valves 20 and 24 to define the second fluid path 36, specifically the meter fluid path 36.1. Again, passive check valves 26, via their respective specific positions within the fluid circuit 16, facilitates such definition of the second fluid path 36, as shown. During dispensing the metered dose of fluid to the collection port 28, as shown in FIG. 2, the dispense fluid path 36.2 also facilitates in venting for example air from the sampling reservoir 30 when the metered dose is dispensed therein, as indicated by the dashed arrow.

In an embodiment, the controller 32 comprises a wireless transceiver for sending and receiving signals to and from the remote computer system 40. In an embodiment, the wireless transceiver comprises a cellular modem configured to establish a dedicated communications protocol 52 between the sampler 10 and the remote computer system 40. However, variations in the manner of establishing the dedicated communications protocol is possible, for example Bluetooth, wi-fi, or the like. As described earlier, such a dedicated communications protocol 52 is important as it obviates reliance on existing networks which may not be readily accessible.

Importantly, the controller 32 performs a number of functions to facilitate operation of the fluid sampler 10. For example, the actuator of the reciprocating piston of the fluid meter 20 is typically controlled by the controller 32 in accordance with the control regime. The controller 32 may also include a sampling reservoir presence sensor 44 configured to sense a presence of a received sampling reservoir 30 at the sampling port 28, with the controller 32 configured to only perform the meter cycle if a sampling reservoir 30 is present to prevent spillage.

In one embodiment, the controller 32 also includes a fluid characteristic sensor 42 which is arranged in the fluid circuit 16 and is responsive to characteristics of the sampled fluid. In the exemplified embodiment, the fluid characteristic sensor 42 is arranged as part of the fluid meter 20, but the skilled addressee is to appreciate that variations hereon are possible and expected. Such fluid characteristic sensor 42 may be responsive to a variety of fluid characteristics including a gamut of tribology characteristics as related to machinery. For example, fluid characteristic sensor 42 may be configured to sense temperature, viscosity, pressure, oxidation, acidity or basicity, permittivity, opacity, impedance, etc. By sensing such fluid characteristics, it is generally possible to determine an operating health of the machinery 8, as known in the art.

In one embodiment, the controller 32 is configured to transmit such sensed fluid characteristics to the remote computer system 40 via the transceiver 38, further facilitating remote fluid sample conditioning monitoring. Similarly, the controller 32 may also be configured to receive an update to the control regime from the remote computer system 40 via the transceiver 38, i.e. changes to the control regime as a software update.

In an embodiment, the control regime generally comprises control functions selectable from a non-exhaustive group consisting of sampling intervals, sampling frequency, volume of metered dose, transmission of sensed fluid characteristics, control errors and sampler health. Accordingly, the control regime generally provides the controller 32 with instructions or directions to perform said controller's functions, including frequency of sampling, dose of fluid captured, sensing and sending sensed fluid characteristics to the remote computer system 40, and the like.

In one embodiment, the flush cycle of the control regime includes the controller 32 sensing the fluid characteristics in the fluid circuit 16 by means of the fluid characteristic sensor 42, with the meter cycle only performed by the controller 32 once a predetermined sensed as fluid characteristic(s), such temperature, is constant for a predetermined period of time. For example, and advantageously, by the control regime configuring the controller 32 to first sense, for example, that a temperature of the fluid flushed through the fluid circuit 16 is stable or constant, e.g. unchanged for 3 seconds, or the like, ensures that a homogenous sample is taken by the meter cycle. Similarly, other fluid characteristics can be sensed for constancy to prevent capturing of contaminated or non-homogenous samples resulting from, for example, build-up of contaminants near the inlet port 12, or the like.

In a further embodiment, the fluid sampler 10 typically comprises a sealed enclosure 46 for housing the various parts. Such an enclosure 46 may include a pressuriser 48, such as an air pump, which is configured to generate a positive air pressure withing said enclosure to impede ingress of contaminants that may contaminate a collected sample. Typically, such a pressuriser 48 may be controllable by the controller 32 as part of the control regime, e.g. as part of the meter cycle, the pressuriser 48 pressurises the enclosure to prevent sample contamination from dust, or the like.

Figure 4:
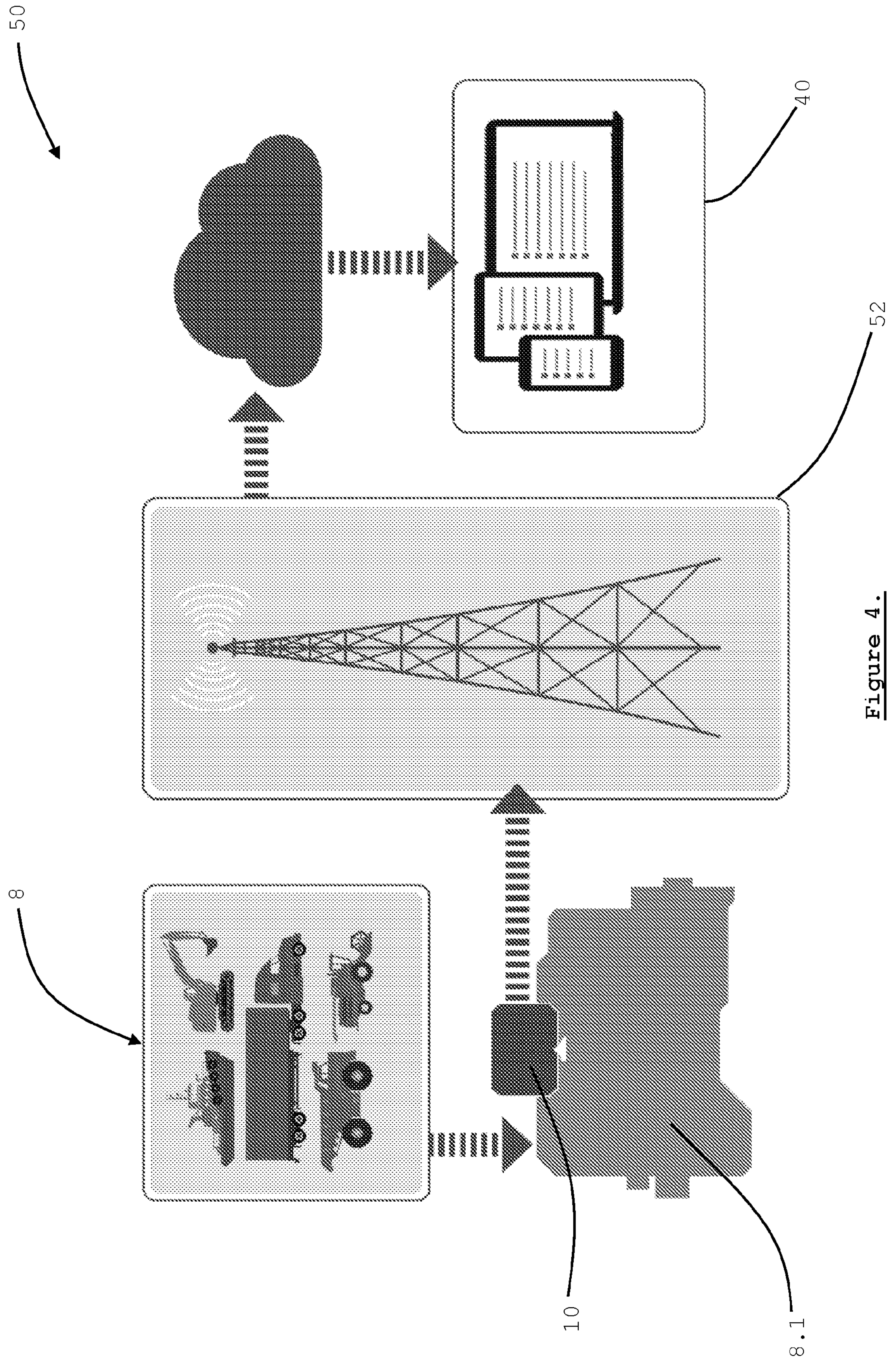
FIG. 4 is a diagrammatic representation of an embodiment of a remote fluid sampling system, in accordance with an aspect of the present invention.

The skilled addressee is to appreciate that the present invention includes an associated remote fluid sampling system 50, as broadly exemplified in FIG. 4. Such a sampling system 50 typically comprises machinery including the remote fluid sampler 10, and the remote computer system 40. The wireless transceiver 38 of the fluid sampler 10 operatively establishes a dedicated communications protocol 52 between the sampler 10 and the remote computer system 40, and the controller 32 of the fluid sampler 10 performs the control regime as described to facilitate flushing of fluid through the fluid circuit 16 of the sampler 10 to allow subsequent collection of a homogeneous fluid sample from the machinery 8, in use.

Applicant believes it particularly advantageous that the present invention provides for a remote fluid sampler 10 and associated fluid sampling system 50 able to address the shortcomings identified above. The fluid circuit 16 also generally obviates the need for valves, check valves and seals that must 'actively' resist fluid pressures to prevent leakages when the sampler is inactive. Sampler 10 also facilitates flushing of fluid circuit 16 to allow homogenous sample collection, as well as being able to sensing fluid characteristics for sending to a remote computer system for logging and analyses.

Optional embodiments of the present invention may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth. In the example embodiments, well-known processes, well-known device structures, and well-known technologies are not described in detail, as such will be readily understood by the skilled addressee.

The use of the terms "a", "an", "said", "the", and/or similar referents in the context of describing various embodiments (especially in the context of the claimed subject matter) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. As used herein, the term "and/or" includes any and all combinations of one or more of the associated listed items. No language in the specification should be construed as indicating any non-claimed subject matter as essential to the practice of the claimed subject matter.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

It is to be appreciated that reference to "one example" or "an example" of the invention, or similar exemplary language (e.g., “such as”) herein, is not made in an exclusive sense. Various substantially and specifically practical and useful exemplary embodiments of the claimed subject matter are described herein, textually and/or graphically, for carrying out the claimed subject matter.

Accordingly, one example may exemplify certain aspects of the invention, whilst other aspects are exemplified in a different example. These examples are intended to assist the skilled person in performing the invention and are not intended to limit the overall scope of the invention in any way unless the context clearly indicates otherwise. Variations (e.g. modifications and/or enhancements) of one or more embodiments described herein might become apparent to those of ordinary skill in the art upon reading this application. The inventor(s) expects skilled artisans to employ such variations as appropriate, and the inventor(s) intends for the claimed subject matter to be practiced other than as specifically described herein.

Any method steps, processes, and operations described herein are not to be construed as necessarily requiring their performance in the particular order discussed or illustrated, unless specifically identified as an order of performance. It is also to be understood that additional or alternative steps may be employed.

The invention claimed is:

1. A remote fluid sampler for sampling fluid, such as oil, from machinery, said sampler comprising:

an inlet and an outlet port via which said sampler is arrangeable in fluid flow communication with said machinery, a fluid circuit defined between said inlet and outlet ports;

a 4-way diverter control valve configured to control a direction of fluid flow along such fluid circuit;

a fluid meter configured to capture a metered dose of fluid from said fluid circuit;

a normally-open (NO) control valve arranged in parallel with a normally-closed (NC) control valve to regulate dynamically fluid flow through the fluid circuit;

a plurality of check valves arranged to regulate passively fluid flow through the fluid circuit;

a sampling port configured to receive a sampling reservoir for receiving a metered dose of fluid; and a controller arranged in signal communication with the fluid meter, 4-way diverter control valve and control valves and configured to perform a user-configurable control regime comprising:

i. a flush cycle by selectively controlling the 4-way diverter control valve and control valves to define a first fluid path along a portion of the fluid circuit which flushes the fluid meter and bypasses the sampling port;

ii. a meter cycle by selectively controlling the fluid meter, 4-way diverter control valve and control valves to define a second fluid path along the fluid circuit which allows the fluid meter to collect fluid from the fluid circuit and thereafter dispense such a metered dose of said collected fluid to the sampling port;

wherein the sampler facilitates flushing of fluid through the fluid circuit to allow collection of a homogeneous fluid sample from the machinery, in use.

2. The remote fluid sampler of claim 1, wherein the controller comprises a wireless transceiver for sending and receiving signals to and from a remote computer system.

3. The remote fluid sampler of claim 2, wherein the wireless transceiver comprises a cellular modem configured to establish a dedicated communications protocol between the sampler and the remote computer system.

4. The remote fluid sampler of claim 2, wherein the controller is configured to receive an update to the control regime from the remote computer system via the transceiver.

5. The remote fluid sampler of claim 1, which comprises a fluid cylinder with a reciprocating piston therein, said piston configured to slidably displace due to fluid pressure in the fluid circuit from the machinery to capture a metered dose of fluid during the meter cycle.

6. The remote fluid sampler of claim 1, which comprises a fluid cylinder with a reciprocating piston therein, an actuator configured to slidably displace said piston in the cylinder to capture a metered dose of fluid.

7. The remote fluid sampler of claim 6, wherein the actuator of the reciprocating piston is controlled by the controller in accordance with the control regime.

8. The remote fluid sampler of claim 1, wherein the fluid meter is controlled by the controller in accordance with the control regime.

9. The remote fluid sampler of claim 1, wherein the controller includes a fluid characteristic sensor arranged in the fluid circuit and configured to be responsive to characteristics of the sampled fluid.

10. The remote fluid sampler of claim 9, wherein the fluid characteristic sensor is responsive to fluid characteristics selected-selectable from a non-exhaustive list consisting of temperature, viscosity, pressure, oxidation, acidity or basicity, permittivity, opacity and impedance.

11. The remote fluid sampler of claim 9, wherein the controller is configured to transmit sensed fluid characteristics to the remote computer system via the transceiver.

12. The remote fluid sampler of claim 9, wherein the flush cycle of the control regime includes the controller sensing the fluid characteristics in the fluid circuit, the meter cycle only performed once predetermined sensed fluid characteristics are constant for a predetermined period of time.

13. The remote fluid sampler of claim 1, wherein the control regime comprises control functions selectable from a non-exhaustive group consisting of sampling intervals, sampling frequency, volume of metered dose, transmission of sensed fluid characteristics, control errors and sampler health.

14. The remote fluid sampler of claim 1, wherein the controller includes a sampling reservoir presence sensor to sense a presence of a received sampling reservoir at the sampling port, the controller configured to only perform the meter cycle if a sampling reservoir is present.

15. The remote fluid sampler of claim 1, wherein the 4-way diverter control valve comprises a 4-way 3-position spool diverter valve.

16. The remote fluid sampler of claim 1, wherein the control valves for dynamic fluid flow regulation comprises solenoid valves.

17. The remote fluid sampler of claim 1, wherein the check valves for passive fluid flow regulation comprises soft-seat check valves.

18. The remote fluid sampler of claim 1, which comprises a sealed enclosure with a pressuriser configured to generate a positive air pressure withing said enclosure to impede ingress of contaminants.

19. The remote fluid sampler of claim 1, wherein the second fluid path, as defined by the controller via the control regime, comprises a meter fluid path which allows the fluid meter to collect fluid from the fluid circuit and a dispense fluid path whereby the fluid meter dispenses such collected fluid to the sampling port.

20. A remote fluid sampling system comprising machinery including a remote fluid sampler in accordance with claim 1; and a remote computer system; wherein a wireless transceiver of said fluid sampler operatively establishes a dedicated communications protocol between the sampler and the remote computer system; and wherein a controller of the fluid sampler performs a control regime to facilitate flushing of fluid through a fluid circuit of the sampler to allow subsequent collection of a homogeneous fluid sample from the machinery, in use.

* * * * *